United States Patent [19]
Henson et al.

[11] Patent Number: 6,069,326
[45] Date of Patent: May 30, 2000

[54] HAND HELD MEASUREMENT INSTRUMENT WITH TOUCH SCREEN DISPLAY

[75] Inventors: John W. Henson; Ronald J. Deschenes, both of Newtown, Conn.; Charles W. Gill, Maysville; Robert E. Hennig, Alto, both of Ga.

[73] Assignee: Dresser Industries, Inc., Dallas, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/814,779

[22] Filed: Mar. 10, 1997

[51] Int. Cl.⁷ .................................................. G08C 21/00
[52] U.S. Cl. .................................... 178/18.01; 178/18.03; 178/18.07
[58] Field of Search ............................... 345/1, 2, 3, 169, 345/172, 173, 178; 178/18.01, 18.03, 18.07

[56] References Cited

U.S. PATENT DOCUMENTS

| | | |
|---|---|---|
| 4,078,257 | 3/1978 | Bagley . |
| 4,679,137 | 7/1987 | Lane et al. ................................ 340/706 |
| 4,703,252 | 10/1987 | Perloff et al. .............................. 324/62 |
| 4,763,356 | 8/1988 | Day et al. . |
| 4,805,089 | 2/1989 | Lane et al. ................................ 364/188 |
| 5,065,611 | 11/1991 | Angelosanto et al. . |
| 5,274,362 | 12/1993 | Potvin ....................................... 345/178 |
| 5,274,363 | 12/1993 | Koved et al. ................................ 345/2 |
| 5,327,163 | 7/1994 | Hashimoto et al. . |
| 5,361,078 | 11/1994 | Caine ........................................ 345/1 |
| 5,363,689 | 11/1994 | Hoffmann et al. . |
| 5,379,057 | 1/1995 | Clough et al. ............................ 345/173 |
| 5,471,226 | 11/1995 | Suzuki et al. ............................ 345/178 |
| 5,487,053 | 1/1996 | Beiswenger et al. . |
| 5,500,717 | 3/1996 | Altrieth, III . |
| 5,543,588 | 8/1996 | Bisset et al. . |
| 5,545,857 | 8/1996 | Lee et al. . |
| 5,684,508 | 11/1997 | Brilman ................................... 345/440 |
| 5,751,276 | 5/1998 | Shih ........................................ 345/178 |

Primary Examiner—Vijay Shankar
Attorney, Agent, or Firm—Haynes & Boone, L.L.P.

[57] ABSTRACT

A system and method for providing a hand held measurement instrument utilizing a touch screen display to provide a flexible and un-cluttered user interface. The measurement instrument includes a controller connected to the touch screen display as well as to a control port and a probe port. The control port supplies screen data for use by the touch screen display as well as control data for use in analyzing measurement signals received from the probe port. The controller retrieves one of the screens to be shown on the touch screen display, the screen including one or more keys. In response to one of the keys being touched, the controller performs a predetermined measurement function. In response to another one of the keys being touched, the controller retrieves another of the screens to be shown on the touch screen display. As a result, the touch screen display allows an ideal number of keys to be available to the user for a particular measurement function. Furthermore, each of the keys is appropriately labeled and positioned.

17 Claims, 3 Drawing Sheets

HAND HELD MEASUREMENT INSTRUMENT WITH TOUCH SCREEN DISPLAY

BACKGROUND OF THE INVENTION

The present invention relates to measurement instruments and, more particularly, to an instrument that includes a touch screen display to provide flexibility as well as ease of use.

Hand held measurement instruments are growing in popularity because of their small size and increasing functionality. In fact, many such instruments can perform several measurement functions, such as measuring temperature and pressure. These multi-function measurement instruments typically have several generic keys that apply to all measurement functions, such as numeric keys, and several function specific keys that are unique to particular measurement functions, such as a ° F./° C. toggle key for the temperature function. However, as the number of measurement functions increases, or as the flexibility of these instruments increases, more and more function specific keys must be added to the instrument. As a result, the instrument becomes very cluttered and confusing, especially in determining which key is used for a particular measurement function.

In an attempt to resolve this confusion and provide an uncluttered, more user-friendly interface, some multi-function measurement instruments include multi-purpose keys that change functions as needed. For example, a row of multi-purpose keys are placed under a liquid crystal device ("LCD") display. The LCD display can provide a label directly above each multi-purpose key to describe the function for that key. These labels, in turn, can be changed as the functionality of the multi-purpose key is changed.

This solution, however, only provides limited help. The main problem is that different measurement functions require different numbers of multi-purpose keys. The measurement instrument must therefore include many different multi-purpose keys, as determined by the measurement function requiring the most such keys. As a result, the instrument once again becomes cluttered with different keys, even for measurement functions that require only a few function specific keys.

Therefore, what is needed is a measurement instrument that supports many different measurement functions but is not cluttered with a vast number of keys. Instead, the number of keys should be limited to that required by a particular measurement function.

Furthermore, what is needed is a measurement instrument that provides a changeable number of keys, such keys being labeled and positioned so that the instrument remains uncluttered and has a user-friendly interface.

SUMMARY OF THE INVENTION

A hand held measurement instrument of the present invention includes a touch screen display to provide a flexible and uncluttered user interface. The measurement instrument also includes a controller connected to the touch screen display as well as to one or more control ports and/or I/O ports. In one embodiment, the measurement instrument supports multiple functions. A control module connected to one of the control ports supplies probes for receiving measurement signals, screen data for use by the touch screen display, and control data for use in analyzing the measurement signals. The controller retrieves one of the screens to be shown on the touch screen display, the screen including one or more keys. In response to one of the keys being touched, the controller may perform predetermined measurement functions, or it may retrieve another of the screens to be shown on the touch screen display. As a result, the touch screen display allows an ideal number of keys to be available to the user for a particular measurement function. Furthermore, each of the keys is appropriately labeled and positioned.

DETAILED DESCRIPTION OF THE PREFERRED EMBODIMENT

Figure 1:
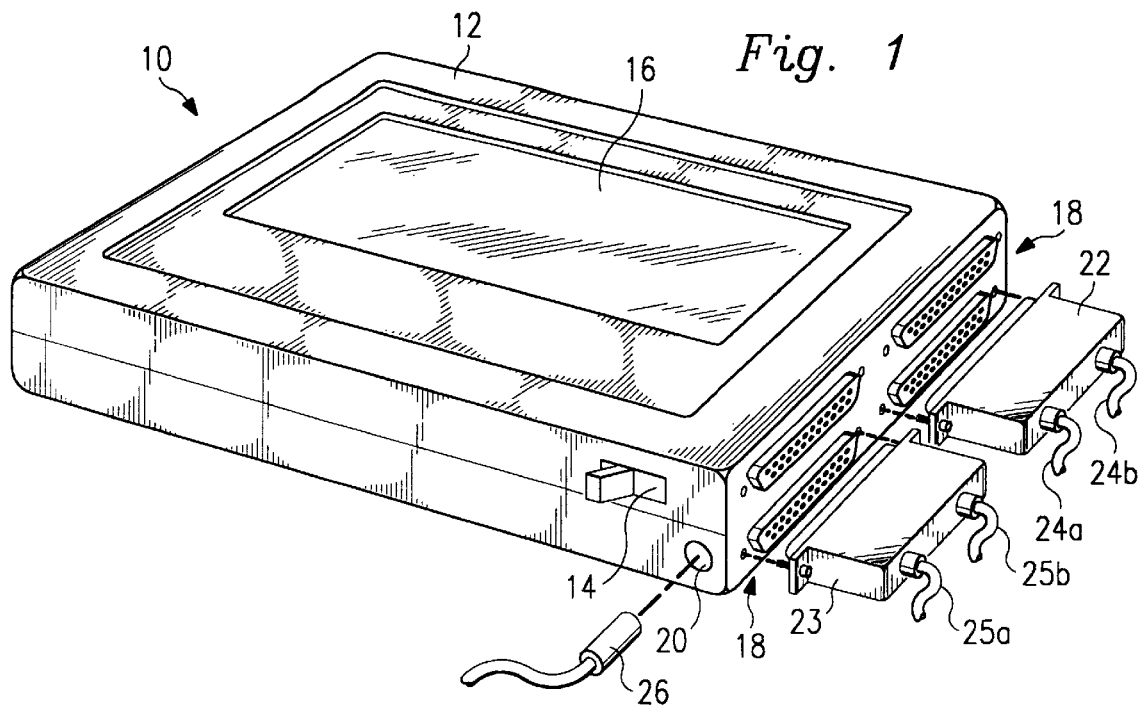
FIG. 1 is a top perspective view of a hand held multi-function measurement instrument embodying features of the present invention.

In FIG. 1, the reference numeral 10 refers to a hand-held measurement instrument embodying features of the present invention. The measurement instrument 10 is a multi-function calibrator ("MFC") that performs pressure calibration and temperature calibration. It is understood, however, that the MFC 10 is exemplary of many different measurement instruments that can benefit from the present invention.

The MFC 10 includes a cabinet 12 having apertures for a power key 14, a touch screen display 16, several control module ports 18 and an input/output ("I/O") port 20. The control module ports 18 are capable of receiving and connecting to one or more control modules, such as control modules 22 and 23. Although not shown, each control module 22, 23 includes software stored in a read only memory ("ROM"). The control module 22 includes software for allowing the MFC 10 to calibrate pressure measurement signals, as well as screen data, discussed in greater detail below. The control module 23 includes software for allowing the MFC 10 to calibrate temperature measurement signals, as well as screen data. It is understood, however, that there may be four control modules similar to the first control module 22, or many different combinations of function specific control modules, with each such control module including different hardware and/or software.

Each control module, in turn is connected to one or more test probes. For example, test probes 24a and 24b are connected to the control module 22 and test probes 25a and 25b are connected to the control module 23. The test probes 24a and 24b are pressure sensors to provide pressure signals to compare with a pressure gauge (not shown) being calibrated while the test probes 25a and 25b are temperature sensors to provide temperature signals to compare with a temperature gauge (also not shown) being calibrated.

The I/O port 20 is capable of receiving and connecting to a digital interface bus 26. The digital interface bus 26 may be used to allow the measurement instrument 10 to interface with a digital computer (not shown). In addition, the I/O port may receive a digital probe (also not shown) to provide a direct digital data connection from the pressure gauge being calibrated.

Figure 2:
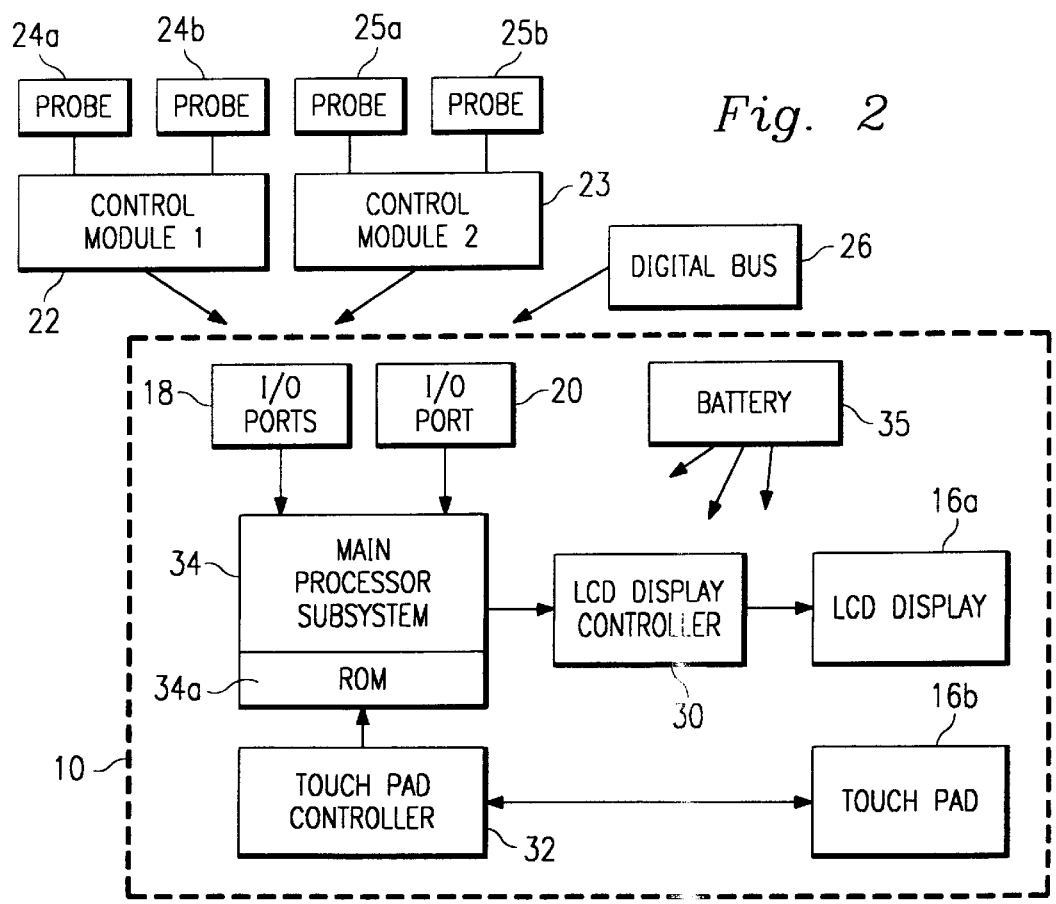
FIG. 2 is a schematic block diagram of the hand held multi-function measurement instrument of FIG. 1.

Referring to FIG. 2, the touch screen display 16 includes a liquid crystal device ("LCD") display 16a and a touch pad 16b. The LCD display 16a is controlled by an LCD display controller 30 and the touch pad 16b is controlled by a touch pad controller 32. Both the display controller 30 and touch pad controller 32 also interface with a main processor subsystem 34. The MFC 10 also includes a battery 35 for supplying power to all the various components.

Figure 3A:
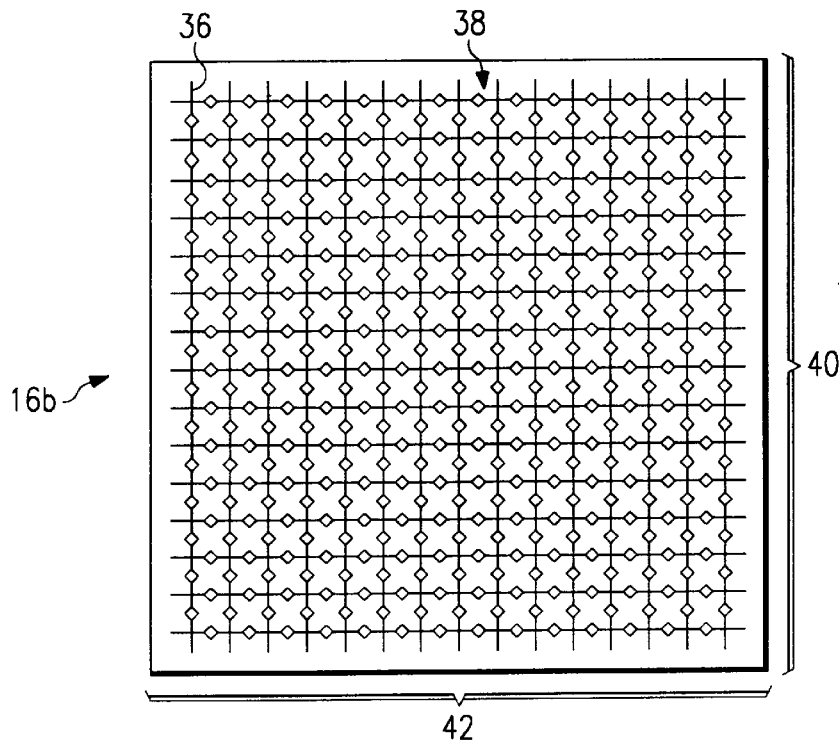
FIGS. 3a and 3b illustrate a touch screen display used by the hand held multi-function measurement instrument of FIG. 1.
Figure 3B:

Referring to FIGS. 3a and 3b, the touch pad 16b has a transparent body 36. Although not visible to a user, the body 36 includes a sensor array 38 disposed therein. When the user touches the body 36, the sensor array 38 provides coordinate data to the touch pad controller 32 indicating a specific row 40 and column 42 on the array. The touch pad 16b is placed on top of the LCD display 16a. Because the body 36 of the touch pad 16b is transparent, the user can directly view any images on the LCD display 16a provided by the LCD display controller 30. In this way, the LCD display 16a can show one or more keys that can be activated by touching the touch pad 16b directly above.

Referring to FIGS. 4a, 4b, 4c and 4d, the LCD display 16a may provide several different screens as needed. For example, the LCD display 16a may show a main menu screen 50, a setup menu screen 52, a pressure calibration screen 54 or a pressure calibration screen with data logging screen 56. The pressure calibration screen 54 also displays a measurement value of "PSI 10". It is understood, however, that various measurement values such as graphs, dials, or "accept/reject" indicators, may also be displayed on the LCD display 16a.

Figure 5:
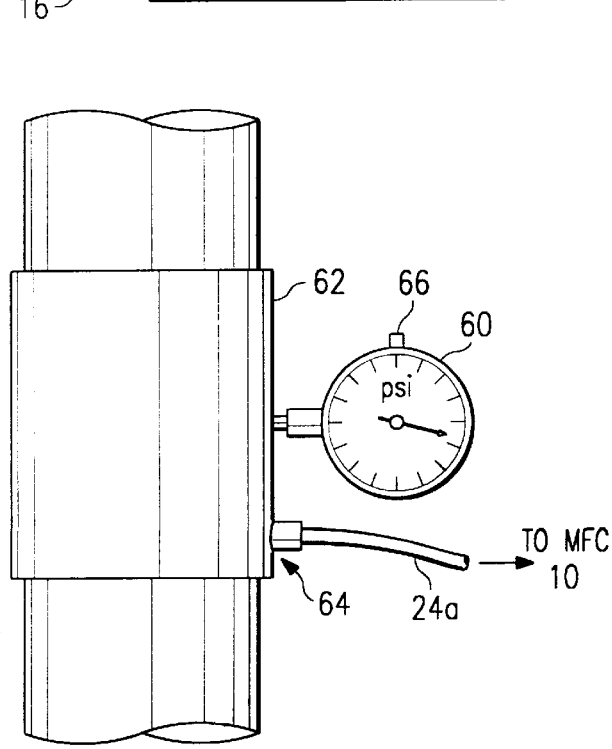
FIG. 5 illustrates a pressure valve being calibrated by the hand held multi-function measurement instrument of FIG. 1.

Referring to FIG. 5, for the sake of example, the MFC 10 is used to calibrate a pressure gauge 60 of a flow valve 62. The flow valve 62 includes an inlet 64 for receiving the test probe 24a (FIG. 1). The pressure gauge 60 includes a calibration knob 66.

Figure 6:
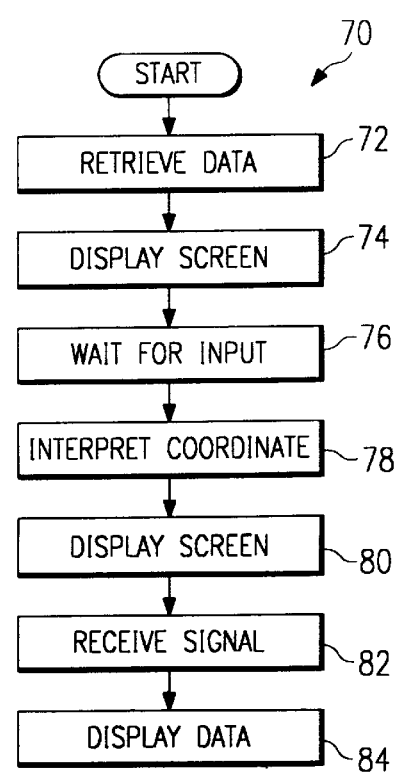
FIG. 6 is a flow chart of a method of operation used by the hand held multi-function measurement instrument of FIG. 1.
Figure 4A:
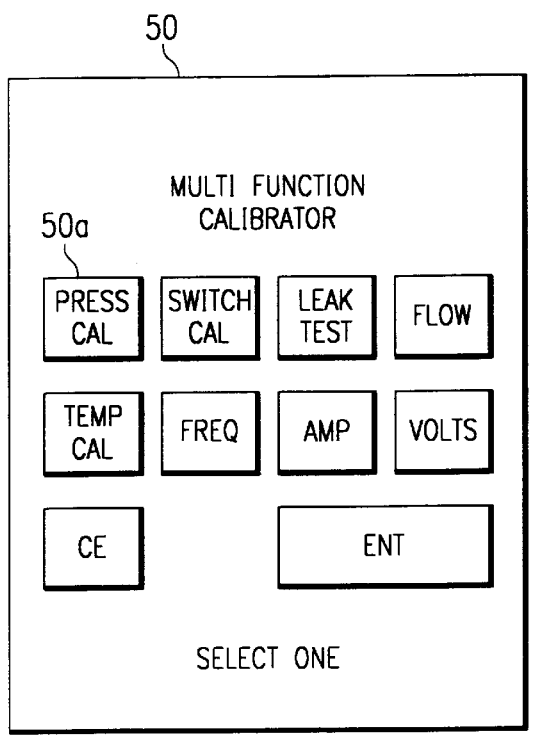
FIGS. 4a, 4b, 4c and 4d illustrate screens capable of being shown on the touch screen display of FIGS. 3a and 3b.
Figure 4B:
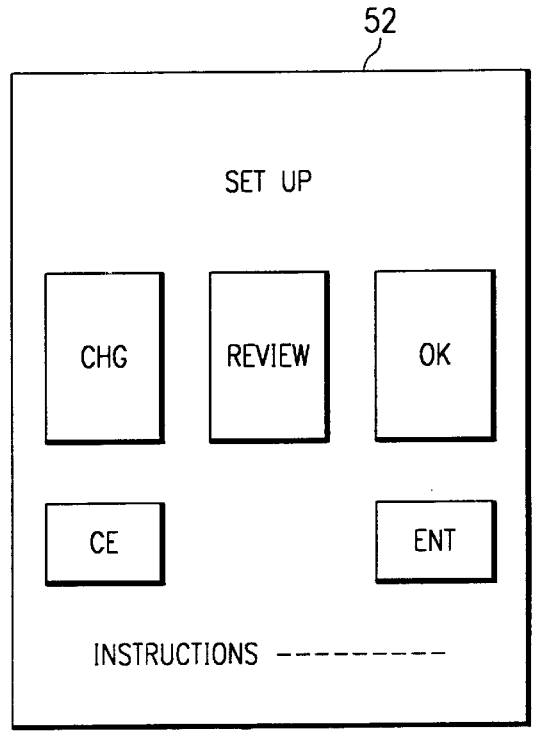
Figure 4C:
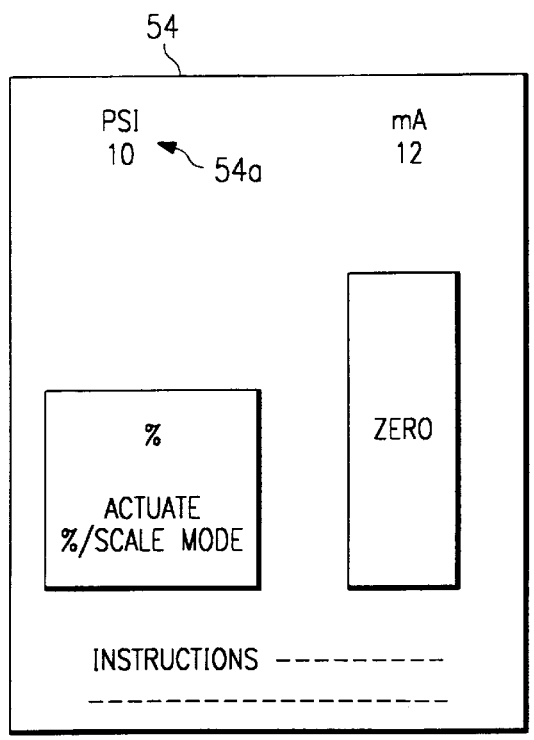
Figure 4D:
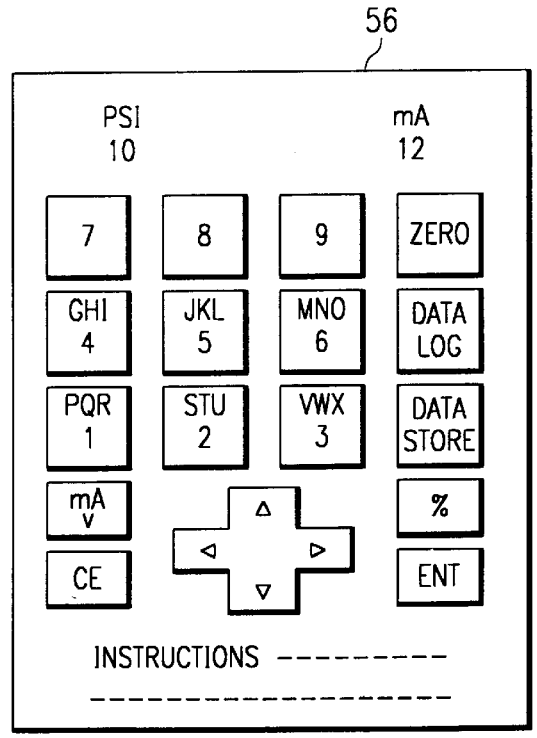

Referring to FIG. 6, to calibrate the pressure gauge 60, the MFC 10 uses a routine 70. To perform the routine 70, the control module 22 and the test probe 24a are inserted into and connected to appropriate I/O ports 18 of the MFC 10 and the power switch 14 is in an "on" position. At step 72, the main processor subsystem 34 of the MFC 10 retrieves screen data for the screens 50, 52, 54, and 56 from the control module 22. To decrease the amount of screen data to be transferred, certain generic screen data, as well as screen layout tools, are stored in a read only memory 34a inside the main processor subsystem 34. At step 74, the main processor subsystem 34 supplies the main menu screen 50 to the LCD display controller 30, which in turn displays the screen on the LCD display 16a.

At step 76, the main processor subsystem 34 waits for input from the touch pad controller 32. When the user presses the touch pad 16b, the touch pad controller 32 provides the coordinate data corresponding to the pressure calibration key 50a. At step 78, upon receipt of the coordinate data, the main processor subsystem 34 determines that the pressure calibration function was selected.

At step 80, in response to receiving the coordinate data from the touch pad controller 32, the main processor subsystem 34 supplies the pressure calibration screen 54 to the LCD display controller 30, which in turn displays the screen on the LCD display 16a.

At step 82, the main processor subsystem 34 receives measurement signals from the test probe 24a that indicate the pressure of the flow valve 62. For the sake of example, the main processor subsystem 34 determines that the measurement value for the pressure is 10 psi. At step 84, the main processor subsystem 34 supplies the 10 psi measurement value to the LCD display controller 30, which in turn displays "PSI 10" on the LCD display 16a. Once the user has received the correct pressure reading (i.e., 10 psi), he may adjust the calibration knob 66 of the pressure gauge 60, accordingly.

A similar routine may be used to determine and calibrate the temperature of the flow valve 62. Also, because the touch screen display 16 is not fixed to any type of readings, the control module 22 may be replaced with a second control module so that the MFC 10 can perform other measurement functions, such as measuring voltage and current. Furthermore, although the routine 70 shows only one level of nesting of the screens 50, 54, it can be adapted to perform different levels of nesting, as required by each measurement function. Further still, the main processor subsystem 34 can also supply instruction data to be displayed on the LCD display 16a.

Additional modifications, changes, and substitutions are intended in the foregoing disclosure. For example, one or more physical keys, such as an "ENTER" key, can be included with the MFC 10 near the touch screen display 16. Furthermore, certain touch screen displays are adapted to react a touch of a wand, while others are adapted to react to a touch of a finger. Accordingly, it is appropriate that the appended claims be construed broadly and in a manner consistent with the scope of the invention.

What is claimed is:

1. A hand-held, multi-function measurement instrument comprising:

a touch screen display;

a port connectable to a first control device;

the first control device for storing a first plurality of screens;

a probe connected to the first control device for making predetermined measurements; and a processor for receiving the first plurality of screens from the first control device and supplying at least one of the first plurality of screens to the touch screen display;

wherein at least one of the screens displays one or more keys for controlling the multi-function measurement instrument.

2. The multi-function measurement instrument of claim 1 wherein the at least one port may receive a second control device storing a second plurality of screens different from the first plurality of screens.

3. The multi-function measurement instrument of claim 1 wherein in response to one key being touched, the processor interprets the measurement signals and supplies a corresponding measurement value to the touch screen display.

4. The multi-function measurement instrument of claim 3 wherein the control device includes a read only memory for use by the processor in interpreting the measurement signals.

5. The multi-function measurement instrument of claim 1 wherein the first plurality of screens are arranged in a nested fashion.

6. The multi-function measurement instrument of claim 5 wherein the first plurality of screens includes a first screen representing a main menu screen and providing first and second keys corresponding to first and second functions, a second screen specific to the first function, and a third screen specific to the second function such that when the first screen is displayed and either the first or second key is touched, the screen corresponding to the touched key is then displayed.

7. The multi-function measurement instrument of claim 1 further comprising a data port for receiving digital data signals from a digital source.

8. The multi-function measurement instrument of claim 1 further comprising a physical key affixed thereto.

9. A hand held measurement instrument comprising:

a touch screen display;

a port for receiving externally supplied plurality of screens and measurement signals from a control module connected to the port and a test probe connected to the port through the control module, respectively; and a processor for receiving through the port the measurement signals from the probe and the plurality of screens from the control module;

wherein the processor supplies one of the plurality of screens to the touch screen display and in response to data supplied from the touch screen display, the processor supplies a second screen of the plurality of screens to the touch screen display, wherein at least one of the screens displays one or more keys for controlling the hand held measurement instrument.

10. The hand held measurement instrument of claim 9 wherein, in response to measurement signals supplied from the port, the processor analyzes the measurement signals and displays a measurement value on the touch screen display.

11. The hand held measurement instrument of claim 9 wherein the plurality of screens also is received through the port.

12. The measurement instrument of claim 9 wherein instructions for how the processor should analyze the measurement signals is also received through the port.

13. The measurement instrument of claim 9 further comprising a digital port for receiving digital measurement signals.

14. A hand held measurement instrument having a touch screen display, the instrument comprising:

a first control module, a test probe connected to the first control module for making a predetermined measurement, and a processor for receiving the measurement from the probe through the first control module, wherein the processor displays the measurement value on the touch screen, and wherein the touch screen has keys for controlling the functions of the hand held measurement instrument.

15. The hand held measurement instrument of claim 14 further comprising:

a second control module, a second test probe connected to the second control module for making a second predetermined measurement, and a second port for receiving the second control module.

16. The hand held measurement instrument of claim 14 further comprising a data port for receiving a digital interface bus for data transfer.

17. The hand held measurement instrument of claim 15 wherein the touch screen key selected determines which control module is functioning, and wherein the functioning control module gives instructions to the processor as to how to analyze the measurement from the corresponding probe.

* * * * *